(12) United States Patent
Kupper et al.

(10) Patent No.: US 6,929,792 B1
(45) Date of Patent: Aug. 16, 2005

(54) MODIFIED DENDRITIC CELLS AND USE THEREFOR

(75) Inventors: Thomas S. Kupper, Weston, MA (US); Ulrich Von Andrian, Boston, MA (US); Caroline Robert, Sceaux (FR)

(73) Assignees: The Brigham & Women's Hospital, Inc., Boston, MA (US); The CBR Institute for Biomedical Research, Inc., Boston, MA (US)

( * ) Notice: Subject to any disclaimer, the term of this patent is extended or adjusted under 35 U.S.C. 154(b) by 0 days.

(21) Appl. No.: 09/540,963

(22) Filed: Mar. 31, 2000

Related U.S. Application Data

(60) Provisional application No. 60/127,423, filed on Apr. 1, 1999.

(51) Int. Cl.$^7$ .................. A61K 48/00; A01N 63/00; C12N 5/00; C12N 15/63; C12N 15/74
(52) U.S. Cl. ............. 424/93.21; 424/93.3; 424/93.71; 424/93.77; 424/93.2; 424/93.1; 435/325; 435/320.1; 435/455; 514/44
(58) Field of Search ............. 424/93.1, 93.2, 424/93.21, 93.3, 93.71, 93.77; 435/326.1, 435/51.5, 455; 514/44

(56) References Cited

FOREIGN PATENT DOCUMENTS

WO     WO 98/46083 A1     10/1998

OTHER PUBLICATIONS

Miller et. al.; Targeted vectors for gene therapy, 1995, FASEB J> 9: 190-199.*
Deonarain, Ligand-targeted receptor-mediated vectors for gene delivery, 1998, Exp. Opin. Ther. Patents 8(1): 53-69.*
Orkin et al.; Report and Recommendations of the Panel to Assess the N IH Investment in Research on Gene Therapy, 1995.*
Ross et al.; Gene Therapy in the United States: A Five-Year Status Report, 1996, Human Gene Therapy 7: 1781-1790.*
Bondanza et al. (1998) J. Leuk. Biol., Suppl. 2, p. 70, abstract F17.*
Whiss et al. (1998) Cell Adh. Comm., vol. 6 (4), 289-300.*
Stoddart et al., *J. Immunol.* 157:5653-5659, 1996.
Von Andrian et al., *Cell* 82:989-999, 1995.
Stein et al. *J. Exp. Med.* 189:37-49, 1999.
Lawrence and Springer, *Cell* 65:859-873, 1991.
Diacovo et al., *Science*, 273: 252-255, 1996.
Von Andrian, *Microcirculation* 3:287-300, 1996.
Mayordomo et al., *Nature Med.* 1:1297-1302, 1995.
Ory et al., *Proc. Natl. Acad. Sci. USA* 93:11400-11406, 1996.
Klein et al., Blood 94(10):398a (1999).
Robert et al., J of Invest. Derm. 112(4):524 (1994).
Diacovo et al., Blood 90(10):567a (1997).

* cited by examiner

*Primary Examiner*—Anne M. Wehbé
(74) *Attorney, Agent, or Firm*—Wolf, Greenfield & Sacks, P.C.

(57) ABSTRACT

The invention provides isolated dendritic cells genetically modified to express a selectin polypeptide, optionally treated with activated platelets or membrane microparticles thereof. The invention also provides isolated platelet modified dendritic cells. Methods for delivering the modified dendritic cells to peripheral lymph nodes and methods for using the modified dendritic cells to stimulate immune responses also are provided. Vaccine compositions containing the modified dendritic cells also are provided.

16 Claims, 1 Drawing Sheet

MODIFIED DENDRITIC CELLS AND USE THEREFOR

RELATED APPLICATIONS

This application claims the benefit of U.S. provisional application Ser. No. 60/127,423, filed Apr. 1, 1999.

GOVERNMENT SUPPORT

This work was funded in part by the National Institutes of Health under grant numbers AI25082-11, AR42689 and HL54936. The government may retain certain rights in this invention.

FIELD OF THE INVENTION

The invention relates to antigen presenting cells which are modified with exogenous binding molecules which bind selectin ligands on endothelial cells.

BACKGROUND OF THE INVENTION

The immune system of a mammal often provides the first line of defense against pathogenic organisms, as well as against tumors. The immune system recognizes antigens expressed by tumor cells or pathogens as foreign, i.e., "non-self". Upon recognition of a non-self antigen, an immune response is mounted against the antigen, resulting in antibodies and/or cytolytic T cells which recognize the antigen. The immune response of a mammal is also responsible for allergy (to antigens known as allergens) and autoimmune disease, which results from inappropriate recognition of host proteins as non-self.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. The interaction of T cells and complexes of HLA/peptide is restricted, requiring a T cell specific for a particular combination of an HLA molecule and a peptide. Another mechanism exists for presentation of non-peptide antigens (such as lipids, glycolipids and carbohydrates) to T cells. This mechanism involves the formation of a complex of the non-peptide antigen and CD1 proteins. If a specific T cell is not present, there is no T cell response even if its partner complex is present. Similarly, there is no response if the specific complex is absent, but the T cell is present. These mechanisms are involved in the immune system's response to foreign materials, in autoimmune pathologies, and in responses to cellular abnormalities.

It has been demonstrated that cytotoxic T lymphocytes provide an effective response against tumor cells. Tumor cells express tumor associated genes. The protein expression products of these genes are processed into peptides which, in turn, are presented by HLA/MHC on cell surfaces, which can lead to lysis of the tumor cells by specific CTLs. The genes are said to code for proteins which are "tumor rejection antigen precursors", and the peptides derived therefrom are referred to as "tumor rejection antigens". Therefore, immunization which increases host cytotoxic T lymphocytes specific for one or more tumor rejection antigens can reduce tumor load in the host. CTL involvement in other desirable immune responses (e.g. against antigens of pathogens) as well as in undesirable immune responses (e.g. against allergens, self antigens and antigens associated with transplanted tissue grafts) is also well known.

Several steps are required for the generation of a specific T cell response, starting with antigen processing and presentation of antigenic peptides by MHC on antigen presenting cells (APCs), followed by T cell priming from signals transmitted through the T cell receptor and through co-stimulatory molecules, such as CD28 and CD40 ligand, resulting in the clonal expansion of T cells.

Dendritic cells (DCs) are potent antigen presenting cells which efficiently stimulate immune recognition of presented peptides. Activation of naive T cells in lymph nodes is mediated exclusively by dendritic cells. A major weakness of current DC immunization approaches is the inability to deliver the DCs directly from blood to secondary lymphoid tissues (including lymph nodes) throughout the body where selectin ligands on endothelial cells are required for homing of blood-borne leukocytes. Thus there is a need to have improved methods and compositions for stimulating immune responses against pathogenic organisms, cellular abnormalities including tumors, and the like.

There is also a need to have improved methods and compositions for reducing inappropriate immune responses, such as found in allergy and autoimmune disease. Reduction of host immune responses is also desirable to reduce allograft transplant rejection by the host.

SUMMARY OF THE INVENTION

It has now been discovered that dendritic cells cultured in vitro do not express sufficient L-selectin, a critical adhesion molecule that permits entry of cells through the lymph node post capillary venule endothelium, for effective targeting of dendritic cells to peripheral lymph nodes. Cells exiting blood into lymph nodes pass through high endothelial venules (HEVs), which are specialized blood vessels which constitutively express carbohydrate-containing L-selectin ligands. For example, naive T cells express L-selectin on their surface which allows them to interact with L-selectin ligands on HEV to bind under flow conditions. The bound T cells then are activated by chemokines in situ and use cell surface integrins to extravasate into lymph nodes. Because they lack sufficient L-selectin expression, cultured dendritic cells cannot exit blood via HEVs directly into lymph node where naive T cells await antigen presentation.

To remedy this deficiency, isolated dendritic cells have been genetically modified to express on their cell surface molecules which bind to L-selectin ligands present on HEVs. Dendritic cells also have been treated with activated platelets which express P-selectin to form platelet modified dendritic cells. The activated platelets serve as a bridge between the cultured dendritic cells and selectin ligands on HEVs. Both genetically modified and platelet modified DCs adhere to lymph node vessel specific ligands in vitro and in vivo.

Thus the invention provides isolated genetically modified dendritic cells, optionally treated with activated platelets or membrane microparticles thereof. The invention also provides isolated platelet modified dendritic cells. Methods for delivering the modified dendritic cells to peripheral lymph nodes and methods for using the modified dendritic cells to stimulate immune responses also are provided. Vaccine compositions containing the modified dendritic cells also are provided.

According to one aspect of the invention, methods for delivery of dendritic cells to a secondary lymphoid tissue of a subject or to a non-lymphoid tissue of a subject where selectin ligands are expressed on endothelial cells are provided. The methods include providing isolated genetically modified dendritic cells which express on the cell surface a selectin polypeptide which includes an endothelial selectin ligand binding portion of a selectin. The binding portion of a selectin is a portion of L-selectin, E-selectin or P-selectin. The methods also include administering the isolated genetically modified dendritic cells to the subject. Preferably the selectin polypeptide is L-selectin, E-selectin or P-selectin.

In certain preferred embodiments, the step of providing isolated dendritic cells includes isolating dendritic cells from the subject and transfecting the isolated dendritic cells with a nucleic acid molecule that encodes the selectin polypeptide. The nucleic acid molecule preferably is an expression vector. Preferred expression vectors included retroviruses, lentiviruses, adenoviruses and lambda bacteriophages. A particularly preferred expression vector is a retrovirus.

The step of providing isolated dendritic cells also can include treating the isolated transfected dendritic cells with isolated activated platelets or membrane microparticles thereof which contain P selectin.

According to another aspect of the invention, methods for delivery of dendritic cells to a secondary lymphoid tissue of a subject or to a non-lymphoid tissue of a subject where selectin ligands are expressed on endothelial cells are provided. The methods include providing isolated dendritic cells, treating the isolated dendritic cells with isolated activated platelets or membrane microparticles thereof which contain P selectin to form platelet modified dendritic cells, and administering the isolated platelet modified dendritic cells to the subject. In some embodiments, the step of providing isolated dendritic cells further comprises culturing the isolated dendritic cells to expand the isolated dendritic cells. In another aspect of the invention, the isolated dendritic cells and the isolated activated platelets or membrane microparticles thereof are not contacted, but the isolated activated platelets or membrane microparticles thereof are administered prior to or concurrently with the isolated dendritic cells.

In certain preferred embodiments of the foregoing methods, the secondary lymphoid tissue is peripheral lymph nodes, appendix or tonsil. In other embodiments, the non-lymphoid tissue where selectin ligands are expressed on endothelial cells is a site of chronic inflammation.

In other preferred embodiments of the foregoing methods, the step of providing isolated dendritic cells further comprises culturing the isolated dendritic cells to expand the isolated dendritic cells.

Preferably the isolated dendritic cells are administered parenterally, especially intraarterially or intravenously.

In the foregoing methods, the step of providing isolated dendritic cells in some embodiments includes culturing the isolated dendritic cells to expand the isolated dendritic cells.

According to still another aspect of the invention, compositions including isolated genetically modified dendritic cells are provided. The dendritic cells express on the cell surface a selectin polypeptide having an endothelial selectin ligand binding portion of L-selectin, E-selectin or P-selectin. Preferred selectin polypeptides are L-selectin, E-selectin and P-selectin.

In preferred embodiments, the amount of the selectin polypeptide expressed on the cell surface is greater than the naturally occurring amount of the selectin expressed on the cell surface in vitro. Preferably the amount of the selectin polypeptide expressed is sufficient to target the genetically modified dendritic cells to secondary lymphoid tissues, including peripheral lymph nodes, or non-lymphoid tissues having selectin ligands expressed on endothelial cells.

In some embodiments the isolated dendritic cells are transfected with a nucleic acid molecule which encodes the selectin polypeptide, and preferably the nucleic acid molecule is an expression vector. Preferred expression vectors include retroviruses, lentiviruses, adenoviruses and bacteriophage lambda, particularly retroviruses.

In other embodiments, the compositions include isolated activated platelets or membrane microparticles thereof which contain P selectin.

According to another aspect of the invention, compositions including isolated dendritic cells and isolated activated platelets or membrane microparticles thereof which contain P selectin are provided.

Vaccine compositions including the foregoing compositions and an antigen also are provided in another aspect of the invention. In certain preferred embodiments, the antigen is a peptide. In other preferred embodiments, the isolated dendritic cells are loaded with the antigen ex vivo, or the isolated dendritic cells are transfected with a nucleic acid molecule which encodes the antigen. In these latter embodiments, the nucleic acid molecule preferably encodes at least two antigens. Preferred antigens include MAGE, MART, LAGE, NY-ESO-1, tyrosinase, PRAME, prostate specific antigen (PSA), BCR-ABL, T cell receptor from T cell tumors, immunoglobulins from B cell tumors, RAS and carcinoembryonic antigen (CEA).

In still other preferred embodiments, the vaccine compositions include at least one adjuvant. In some of these preferred embodiments, the adjuvant is a nucleic acid molecule encoding a polypeptide adjuvant transfected into the isolated dendritic cells. Certain preferred adjuvants stimulate an immune response to the antigen, including IL-12, GM-CSF, CD40, CD80 (B7-1) and CD86 (B7-2). Other preferred adjuvants inhibit an immune response to the antigen, including IL-10 and TGF-β. Still other preferred adjuvants orient an immune response to certain lymphocyte subsets, including IL-4 (Th2) and interferon-γ (Th1).

According to yet another aspect of the invention, methods for stimulating or inhibiting an immune response to an antigen in a subject are provided. The methods include administering to the subject an appropriate composition selected from the foregoing vaccine compositions.

Methods for testing the immunogenicity of an antigen also are provided. The methods include providing a subject, administering to the subject one of the foregoing vaccine composition (except those vaccine compositions which inhibit an immune response), wherein the immunogenicity of the antigen is not known, and determining the immune response of the subject to the antigen.

Also provided are methods for making the compositions and vaccine compositions described herein. The methods include in some embodiments isolating dendritic cells and introducing into the dendritic cells a selectin polypeptide, an antigen, a cytokine, an adjuvant, a nucleic acid molecule which encodes any of the foregoing, or combinations of the foregoing.

Kits which include the compositions also are provided, optionally including instructions for administering the compositions to modulate an immune response. The kits can also include other components, such as adjuvants, cytokines, antigens, and the like.

Still other aspects of the invention provide for the use of the foregoing compositions in the preparation of a medicament. Preferred medicaments include those which are useful in modulation of an immune response in a subject.

These and other objects of the invention will be described in further detail in connection with the detailed description of the invention.

DETAILED DESCRIPTION OF THE INVENTION

Figure 1:
FIG. 1 is a digitized low-voltage scanning electron micrograph showing delineating E/L-selectin expression on the surface of a murine bone marrow-derived dendritic cell at 80,000× magnification.

It has now been discovered that cultured dendritic cells (DCs) can be modified to enable the DCs to enter peripheral lymph nodes by extravasation through high endothelial venules (HEVs). Although not wishing to be bound by any particular theory or mechanism, it is believed that a principal reason why cultured DCs are unable to reach peripheral lymph nodes is because cultured DCs lack sufficient L-selectin expression. This unexpected finding provides the basis for designing methods for overcoming this deficiency, namely, by genetically modifying isolated dendritic cells to express a selectin polypeptide which binds a selectin ligand on endothelial cells. Alternatively, entry of cultured DCs into peripheral lymph node (PLN) also can be made possible by treating isolated dendritic cells with activated platelets or a derivative thereof which includes P-selectin protruding from a surface where it is accessible for binding by dendritic cells and endothelial selectin ligand on HEVs. According to yet another aspect of the invention, DCs also can be both genetically modified and treated with activated platelets or derivatives thereof. Therefore the invention disclosed herein provides the unexpected result that augmentation of selectin polypeptides on the surface of cultured dendritic cells can alter the ability of the DCs to enter peripheral lymph nodes, thereby enhancing antigen presentation. Thus the invention provides methods for delivering or targeting antigen presenting cells to peripheral lymph nodes, methods for modulating an immune response to an antigen presented by dendritic cells, and compositions useful therefor.

As used herein, a "selectin polypeptide" is a polypeptide which includes a portion of a selectin molecule which is capable of binding selectively to a selectin ligand on endothelial cells. Such selectin polypeptides include L-selectin, E-selectin, P-selectin, including non-cleavable forms of L-, E- and P-selecting, such as those having mutated protease cleavage sites (see, e.g., Stoddart et al., *J. Immunol.* 157: 5653–5659, 1996), chimeric selectin molecules, e.g. E/L-selectin (von Andrian et al., *Cell* 82:989–999, 1995; Stein et al. *J. Exp. Med.* 189:37–49, 1999), and functional variants of the foregoing which retain selectin binding properties.

As used herein, "selectin ligands on endothelial cells" include molecules present on the surface of high endothelial venules which bind L-selectin. Selectin ligands on endothelial cells in some instances are known as peripheral node addressins (PNAds). L-selectin recognizes by selective binding several glycoprotein ligands, including GlyCAM-1 (Sgp50), CD34 (Sgp-90), and Sgp200, present on the high endothelial venules of the peripheral lymph nodes.

As used herein, an "endothelial selectin ligand binding portion of a selectin" is that portion of a selectin polypeptide which is necessary and sufficient for binding to a selectin ligand on endothelial cells. Binding portions include extracellular fragments of selectins, optionally fused to other polypeptides, mutated variant selectin polypeptides which retain the ability to bind endothelial selectin ligands, and the like. The endothelial selectin ligand binding portions of selectins can be identified by standard methods of molecular biology and immunology. For example, extracellular fragments of a selectin polypeptide can be prepared by deletion of portions of a nucleic acid encoding the selectin polypeptide using techniques such as PCR, exonuclease digestion, restriction endonuclease digestion to prepare fragments of the nucleic acid molecules, and then cloning the extracellular fragments. Substitutions in the amino acid sequence of a selectin polypeptide to produce functionally equivalent variants of the selectin polypeptide preferably are conservative substitutions, and typically are made by alteration of a nucleic acid encoding the selectin polypeptide. Such substitutions can be made by a variety of methods known to one of ordinary skill in the art. For example, amino acid substitutions may be made by PCR-directed mutation, site-directed mutagenesis according to the method of Kunkel (*Proc. Natl. Acad. Sci. USA.* 82: 488–492, 1985), or by chemical synthesis of a gene encoding a selectin polypeptide. The activity of functionally equivalent fragments of selectin polypeptides can be tested by cloning the gene encoding the altered selectin polypeptide into a bacterial or mammalian expression vector, introducing the vector into an appropriate host cell, expressing the altered selectin polypeptide, and testing for a functional capability of the selectin polypeptides as disclosed herein. Such fragments or variants can then be tested for binding to endothelial selectin ligands using a variety of assays well known in the art, including capillary flow assays (von Andrian et al., *Cell* 82:989–999, 1995), parallel plate flow chamber assays (Lawrence and Springer, *Cell* 65:859–873, 1991; Diacovo et al., *Science,* 273: 252–255, 1996), intravital microscopy (von Andrian, *Microcirculation* 3:287–300, 1996) and the like.

As used herein with respect to dendritic cells, "expand" means to increase the number of dendritic cells in a population by culturing the population of dendritic cells or progenitors of dendritic cells. Preferably DCs are expanded by culturing in vitro under defined culture conditions, such as in medium containing cytokines, growth factors and other nutrients required for DC proliferation and/or maturation.

As used herein, "transfect" or "transfection" means the introduction of one or more exogenous nucleic acids into a cell. Transfection includes introduction of naked nucleic acids such as plasmids by standard physical and chemical transfection techniques, including calcium phosphate precipitation, dextran sulfate precipitation, electroporation, liposome-mediated nucleic acid transfer, ballistic methods such as particle bombardment, etc. Transfection also includes introduction of nucleic acids into cells by biological methods, including viral transduction or infection (receptor-mediated and non-receptor-mediated).

In certain embodiments, isolated dendritic cells are treated (i.e., contacted in vitro, ex vivo, in vivo) with isolated activated platelets or membrane microparticles thereof under conditions which permit binding of the activated platelets or microparticles to the dendritic cells. Activated platelets express cell surface P-selectin, which binds to the cell-surface mucin P-selectin glycoprotein ligand-1 (PSGL-1) of dendritic cells. Methods for activating platelets are well known in the art, including contacting isolated platelets with thrombin or thrombin receptor activating protein (TRAP). Membrane fractions of activated platelets, such as membrane microparticles, which include cell surface P-selectin also can be used for treating dendritic cells. The activated platelets or platelet membrane microparticles bound to the dendritic cells also bind to endothelial selectin ligands present on high endothelial venules. Thus, the activated platelets or platelet membrane microparticles serve a targeting function for the isolated DCs, presumably in the same way that DC cell surface selectin expression does. In addition to the activated platelets or membrane microparticles thereof, one can use other particles containing the appropriate binding molecules to serve as a bridge between the dendritic cells and endothelial selectin ligands, such as membrane vesicles (e.g. liposomes) having surface P-selectin, L-selectin, E-selectin and/or endothelial selectin ligand binding chimeras thereof. The requirements for such targeting particles are that they include (1) molecules that bind dendritic cells (e.g., P-selectin binding of PSGL-1 on DC), and (2) molecules that bind a selectin ligand on HEV (e.g., L-selectin, E-selectin, P-selectin, E-selectin/L-selectin chimeras or P-selectin/L-selectin chimeras).

In certain embodiments, isolated dendritic cells are loaded with one or more antigens. An antigen, as used herein, includes any molecule presented to T cells by dendritic cells, which preferably are antigenic peptides, lipids, carbohydrates, glycolipids, or other small biological molecules. As used herein, "loaded" or "loading" means contacting dendritic cells, preferably ex vivo, with antigen for presentation by MHC molecules or CD1 molecules. In some embodiments, the dendritic cells can be treated prior to loading to remove bound peptides from MHC molecules, e.g., existing cell-surface MHC class I molecules. In other embodiments, antigen is contacted with the dendritic cells for uptake by the DCs, degradation and presentation by MHC molecules. In all embodiments, dendritic cells that are loaded with antigen display on the cell surface complexes of MHC molecules or CD1 molecules and antigen for presentation to T cells.

Presentation of certain antigens by dendritic cells also can be induced by transfecting the DCs with nucleic acid molecules which encode one or more peptide antigens. The encoded antigen may be an entire protein, of which only a small portion is antigenic (e.g., an antigenic peptide), or the antigen may be a fragment of a protein, such as an antigenic peptide. Polypeptides which include more than an antigenic peptide will be processed by the DC to the appropriate size for presentation by MHC molecules.

Antigens which are loaded as polypeptides or transfected as nucleic acid can include more than one antigen linked together (polytope), as described in greater detail below.

As used herein, "isolated" means separated from its native environment and present in sufficient quantity to permit its identification or use. As used herein with respect to cells, isolated means removed from other leukocytes present in a tissue such as blood, bone marrow, etc. As used herein, "cultured" dendritic cells are cells expanded in vitro from precursor cells. Isolated and/or cultured DCs preferably are substantially pure, but need not be for the methods and compositions of the invention. Substantially pure populations of dendritic cells can be prepared by techniques well known in the art including immunoaffinity purification using chromatography or magnetic separation schemes, gradient density centrifugation and the like. Dendritic cells which are stimulated to differentiate from a purified population of precursor cells also are considered substantially pure.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein, isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

In general, ex vivo immunotherapy involves the introduction in vitro of a nucleic acid which encodes an antigen into a cell(s) of a subject, and returning the genetically engineered cell(s) to the subject to stimulate an immune response. In ex vivo immunotherapy using dendritic cells, dendritic cell precursors are removed from a subject for in vitro differentiation and expansion. Nucleic acids encoding endothelial selectin ligand binding polypeptides, antigens or antigen precursors, cytokines and/or detectable markers are introduced (i.e., transduced or transfected) into the cells in vitro. Typically, the modified cells are then expanded in culture before being reimplanted into a subject. As used herein, "subject" means a mammal, including a human, a non-human primate, a sheep, a goat, a horse, a cow, a dog, a cat, and a rodent. The preferred subject is a human.

The compositions and methods of the invention are useful for modulating the responsiveness of a subject's immune system to one or more antigens, e.g. by inducing increased production of cytotoxic T lymphocytes which recognize the antigens or by inducing tolerance of the antigens. This is useful for modulating a subject's immune response for the treatment of tumors or pathogenic infections (increased immune response), or for treatment of autoimmune diseases, allergy, or transplantation (decreased immune response).

The invention is not limited in utility to human immunotherapy, but also provides a method for assessing the effects of immunosuppressive agents in mammalian models such as primates, pigs, sheep, dogs, rodents, and cows. The invention also provides an improved method for testing the effectiveness of antigenic peptides in a mammal. A series of peptides can be administered to the group of mammals as immunizations. The series of peptides can include variants of recognized antigenic peptides and the immune response of each of these variants can thus be assessed to determine the optimal amino acid sequence of immune response boosting peptides. Modifications to the peptides can be made based on known parameters of HLA binding affinity described herein, or randomly, and tested for immunogenic potential by the same methodology. In vitro uses also will be known to one of ordinary skill in the art, including presentation of antigen to T cells for in vitro maturation and stimulation protocols.

Exemplary tumor associated peptide antigens that can be expressed to induce or enhance an immune response are derived from tumor associated genes and encoded proteins including MAGE proteins, MART, LAGE, NY-ESO-1, tyrosinase, PRAME, prostate specific antigen (PSA), BCR-ABL, immunoglobulins from B cell tumors, T cell receptors from T cell tumors, RAS oncogene products, carcinoembryonic antigen (CEA), mutated p53, Melan-A, tyrosinase-related protein-1 and the like.

Other examples will be known to one of ordinary skill in the art (for example, see Coulie, Stem Cells 13:393–403, 1995), and can be used in the invention in a like manner as those disclosed herein.

Antigens that are characteristic of pathogens include antigens derived from viruses, bacteria, parasites or fungi. Examples of important pathogens include Vibrio cholerae, enterotoxigenic Escherichia coli, rotavirus, Clostridium difficile, Shigella species, Salmonella typhi, parainfluenza virus, influenza virus, Streptococcus pneumoniae, Borella burgdorferi, HIV, Streptococcus mutans, Plasmodium falciparum, Staphylococcus aureus, rabies virus and Epstein-Barr virus.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

Bacteria in general include but are not limited to: P. aeruginosa; E. coli; Klebsiella sp.; Serratia sp.; Pseudomonas sp.; P. cepacia; Acinetobacter sp.; S. epidermis; E. faecalis; S. pneumoniae; S. aureus; Haemophilus sp.; Neisseria sp.; N. meningitidis; Bacteroides sp.; Citrobacter sp.; Branhamella sp.; Salmonella sp.; Shigella sp.; S. pyogenes; Proteus sp.; Clostridium sp.; Erysipelothrix sp.; Lesteria sp.; Pasteurella multocida; Streptobacillus sp.; Spirillum sp.; Fusospirocheta sp.; Treponema pallidum; Borrelia sp.; Actinomycetes; Mycoplasma sp.; Chlamydia sp.; Rickettsia sp.; Spirochaeta; Legionella sp.; Mycobacteria sp.; Ureaplosma sp.; Streptomyces sp.; Trichomoras sp.; and P. mirabilis.

Parasites include but are not limited to: Plasmodium falciparum, P. vivax, P. ovale, P. malaria; Toxoplasma gondii; Leishmania mexicana, L. tropica, L. major, L. aethiopica, L. donovani; Trypanosoma cruzi, T. brucei; Schistosoma mansoni, S. haematobium, S. japonium; Trichinella spiralis; Wuchereria bancrofti; Brugia malayi; Entamoeba histolytica; Enterobius vermiculoarus; Taenia solium, T. saginata; Trichomonas vaginatis, T hominis, T. tenax; Giardia lamblia; Cryptosporidium parvum; Pneumocytis carinii; Babesia bovis, B. divergens, B. microti; Isospora belli, I. hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchisfelineus, O. viverrini; Fasciola hepatica; Sarcoptes scabiei; Pediculus humanus; Phthirius pubis; and Dermatobia hominis.

Fungi in general include but are not limited to: Cryptococcus neoformans; Blastomyces dermatitidis; Ajellomyces dermatitidis; Histoplasma capsulatum; Coccidioides immitis; Candida species, including C. albicans, C. tropicalis, C. parapsilosis, C. guilliermondii and C. krusei; Aspergillus species, including A. fumigatus, A. flavus and A. niger; Rhizopus species; Rhizomucor species; Cunninghammella species; Apophysomyces species, including A. saksenaea, A. mucor and A. absidia; Sporothrix schenckii; Paracoccidioides brasiliensis; Pseudallescheria boydii; Torulopsis glabrata; and Dermatophytes species.

Specific examples of antigens characteristic of a pathogen include: the influenza virus nucleoprotein (residues 218–226, Fu et al., J. Virol. 71:2715–2721, 1997), antigens from Sendai virus and lymphocytic choriomeningitis virus (An et al., J. Virol. 71:2292–2302, 1997), the E1 protein of hepatitis C virus (Bruna-Romero et al., Hepatology 25:470–477, 1997), the virus envelope glycoprotein gp160 of HIV (Achour et al., J. Virol. 70: 6741–6750, 1996), amino acids 252–260 or the circumsporozite protein of Plasmodium berghei (Allsopp et al., Eur. J. Immunol. 26:1951–1958, 1996), the infleunza A virus nucleoprotein (residues 366–374, Nomura et al., J. Immunol. Methods 193:4149, 1996), the listeriolysin O protein of Listeria monocytogenes (residues 91–99, An et al., Infect. Immmun. 64:1685–1693, 1996), the E6 protein (residues 131–140, Gao et al., J. Immunol. 155:5519–5526, 1995) and E7 protein (residues 21–28 and 48–55, Bauer et al., Scand. J. Immunol. 42:317–323, 1995) of human papillomavirus type 16, the M2-protein of respiratory syncytial virus (residues 82–90 and 81–95, Hsu et al., Immunology 85:347–350, 1995), the herpes simplex virus type 1 ribonucleotide reductase (Salvucci, et al., J. Virol. 69:1122–1131, 1995) and the rotavirus VP7 protein (Franco et al., J. Gen. Virol. 74:2579–2586, 1993).

Administration of antigens via modified and/or treated dendritic cells with certain cytokines which induce tolerance (e.g., interleukin-10, TGF-β) is useful for reducing immune responses to those antigens. This is useful in the treatment of allergic responses and autoimmune diseases, as well as in treating allograft rejection.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include: the major horse allergen Equ c1 (Gregoire et al., J. Biol. Chem. 271:32951–32959, 1996), the Hor v 9 pollen allergen from barley (Astwood et al., Gene 182:53–62, 1996), the major allergen of the domestic cat, Fel d 1 (Counsell et al., J. Allergy Clin. Immunol. 98:884–894, 1996), a major latex allergen, Hev b 5 (Salter et al., J. Biol. Chem. 271:25394–25399, 1996), a major allergen of salmon, Sal s 1 (Lindstrom et al., Scand. J. Immunol. 44:335–344, 1996), allergens of the house dust mite, B. tropicalis (Carabello et al., J. Allergy Clin. Immunol. 98:573–579, 1996; Der p 2, Chua et al., Clin. Exp. Allergy 26:829–837, 1996; Der p 2, Harris et al., Int. Immunol. 9:273–280, 1997), major allergens of velvet grass, Hol 1 1 and Hol 1 5 (Schramm et al., Int. Arch. Allergy immunol. 110:354–363, 1996), a major allergen of ryegrass, Lol p 9 (Blaher et al., J. Allergy Clin. Immunol. 98:124–132, 1996), the predominant allergen of bovine dander, BDA20 (Mantyjarvi et al., J. Allergy Clin.

*Immunol.* 97:1297–1303, 1996), a major allergen of Kentucky bluegrass pollen, rKBG60 (Zhang et al., *Immunology*, 87:283–290, 1996), and the hornet venom allergen Dol m 5 (King et al., *J. Allergy Clin. Immunol.* 99:630–639, 1997).

Examples of antigens characteristic of autoimmune disease include: antigens from human myelin basic protein (residues 110–118), proteolipid protein (residues 80–88), myelin-associated protein (residues 287–295, 509–517, 556–564) in multiple sclerosis (Tsuchida et al. *Proc. Natl. Acad Sci USA* 91:10859–10863, 1994), the islet cell antigen ICA69 in diabetes (Karges et al., *Biochim. Biophys. Acta* 1360:97–101, 1997), the protein L7 in rheumatic diseases such as systemic lupus erythematosus, rheumatoid arthritis, and systemic sclerosis (Neu et al., *Arthritis Rheum.* 40:661–671, 1997), two peptides from human acetylcholine receptor alpha-subunit, p195–212 and p259–271 in myasthenia gravis (Katz-Levy et al., *Proc. Natl. Acad. Sci. USA* 94: 3200–3205, 1997), the nuclear autoantigen La (SS-B) protein (Bachmann et al., *J. Autoimmun.* 9:747–756, 1996) and the 52-kd Ro(SS-A) protein (Dorner et al., *Hepatology* 24:1404–1407, 1996) in Sjogren's syndrome, and cytochrome P450IID6, the main target antigen of LKM-1 antibody-positive type II autoimmune hepatitis (Lohr et al., *Hepatology* 24:1416–1421, 1996). Other autoimmune antigens will be known to one of ordinary skill in the art.

Other peptide antigens can be identified according to methods used in the foregoing references which describe antigens of tumors, pathogens, allergens and autoimmune disease. Standard references in the art (e.g., *Remington's Pharmaceutical Sciences*, 18th edition, 1990) provide modes of administration and formulations for delivery of immunogens with adjuvant or in a non-adjuvant carrier.

As noted previously, antigens can be provided as polypeptides, peptides (i.e. in a form and length which can be bound and presented by MHC molecules), nucleic acid molecules which encode peptide antigens, lipids, carbohydrates, glycolipids, or other small biological molecules. Especially preferred are nucleic acids encoding a series of antigenic epitopes, known as "polytopes". The epitopes can be arranged in sequential or overlapping fashion (see, e.g., Thomson et al., *Proc. Natl. Acad. Sci. USA* 92:5845–5849, 1995; Gilbert et al., *Nature Biotechnol.* 15:1280–1284, 1997), with or without the natural flanking sequences, and can be separated by unrelated linker sequences if desired. The polytope is processed to generated individual epitopes which are recognized by the immune system for generation of immune responses.

Thus, for example, several HLA class I and HLA class II antigens can be combined (e.g. by preparation of hybrid nucleic acids or polypeptides) to form "polytopes", according to standard procedures of molecular biology. Polytopes comprising two or more potentially immunogenic or immune response stimulating peptides can be joined together in various arrangements (e.g. concatenated, overlapping). The polytope (or nucleic acid encoding the polytope) can be administered in vaccination protocols using the dendritic cells disclosed herein, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13): 5845–5849, 1995; Gilbert et al., *Nature Biotechnol.* 15(12): 1280–1284, 1997; Thomson et al., *J. Immunol.* 157(2): 822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known, for example, that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Likewise, combinations of pathogen antigens can be made to induce protective immune responses against a plurality of pathogens.

Polytopes can be introduced to a patient in need of such treatment as polypeptide structures, or via the use of nucleic acid delivery systems known in the art (see, e.g., Allsopp et al., *Eur. J. Immunol.* 26(8): 1951–1959, 1996). Adenovirus, retroviruses, adeno-associated virus, plasmids, bacteria, etc. can be used in such delivery. One can test the polytope delivery systems in mouse models to determine efficacy of the delivery system. The systems also can be tested in human clinical trials.

As part of the immunization protocols, substances which modulate the immune response may be administered with nucleic acid or peptide components of a vaccine. Such immune response modulating compounds are referred to herein as "adjuvants". Adjuvants of many kinds are well known in the art; specific examples include MPL, a congener obtained after purification and acid hydrolysis of *Salmonella minnesota* Re 595 lipopolysaccharide, saponins including QS21, a pure QA-21 saponin purified from *Quillja saponaria* extract, DQS21, described in PCT application WO96/33739 (SmithKline Beecham), vitamin E and various water-in-oil emulsions prepared from biodegradable oils such as squalene and/or tocopherol.

Cytokines are also useful in vaccination protocols as adjuvants. Many cytokines useful as a result of their lymphocyte regulatory properties will be known to one of ordinary skill in the art, including interleukin-12 (IL-12) which has been shown to enhance the protective effects of vaccines (Science 268: 1432–1434, 1995), GM-CSF and IL-18. Adjuvants which inhibit the immune response are useful in vaccination protocols for tolerization to antigens. Such adjuvants include factors such as IL-10 (see, e.g., Steinbrink et al., *J. Immunol.* 159:4772–80, 1997; Takayama et al., *Transplantation* 66:1567–74, 1998) and TGF-β.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Natl. Acad. Sci. USA* 95:6284–6289, 1998). In addition, a combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). The use of anti-CD28 antibodies to directly stimulate T cells could also be considered.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.,* 158:637–642, 1997; Fenton et al., *J Immunother.,* 21:95–108, 1998).

Lymphocyte function associated antigen-1 (LFA-1) is expressed on leukocytes and interacts with ICAM-1 (CD54) expressed on APCs. This interaction induces T cell IL-2 and IFN-gamma production and can thus complement but not substitute, the B7/CD28 costimulatory interaction (Fenton et al., 1998). ICAM-1 is thus a further example of a costimulatory molecule that could be provided in a vaccination protocol in the various ways discussed above for B7.

Still other examples of molecules that could be provided to dendritic cells in a vaccination protocol are chemokine receptors including CC chemokine receptor 7 (CCR7), which is a receptor for secondary lymphoid-tissue chemokine (SLC) and EBI 1 ligand chemokine (ELC).

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The cultured dendritic cells described herein can be assayed for expression of these molecules, and supplemented if necessary by, e.g., transfection of appropriate nucleic acids, such as by nucleic acid (naked DNA) immunization (Kim et al., *Nature Biotechnol.* 15:7:641–646, 1997) or recombinant viruses (Wendtner et al., *Gene Ther.* 4:726–735, 1997). These systems are all amenable to the construction and use of expression cassettes for the coexpression of B7 or other stimulatory molecules with other molecules of choice such as the antigens or fragment(s) of antigens discussed herein (including polytopes) or cytokines. These delivery systems can be used for induction of the appropriate molecules in vitro and for in vivo vaccination situations.

The use of anti-CD40 antibodies to stimulate DCs directly, would be expected to enhance a response to antigens which are normally encountered outside of an inflammatory context. Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen loaded DC based therapies or in situations where Th epitopes have not been defined within known antigen precursors.

As used herein, antigen embraces a naturally selected antigenic molecule (peptide, glycolipid, other small molecules, etc.) presented by MHC or CD1 molecules, as well as variants of the naturally selected antigenic molecules which can be prepared according to methods known in the art and disclosed herein. For example, peptide antigens administered according to the methods described herein can have the amino acid sequence of a naturally processed antigenic peptide. Alternatively, modifications can be made to the amino acid sequence to enhance binding to HLA for presentation to a subject's immune system, while retaining the ability to induce CTLs which recognize the naturally processed peptide. The portions of HLA binding peptides important for binding activity are known (see, e.g., Parker et al., *J. Immunol.* 149:3580–3587, 1992). Variant antigenic peptides which bind more tightly to HLA molecules have been found to be more immunogenic (Parkhurst et al., *J. Immunol.* 157:2539–2548, 1996; Bakker et al., *Int. J. Cancer* 70:302–309, 1997). A general protocol for modification of HLA binding peptides has been suggested by Parker et al. (*J. Immunol.* 152:163–175, 1994). Thus one of ordinary skill in the art, with only routine experimentation, can design synthetic variant peptides which can be administered to induce an immune response in a host. The methods disclosed herein provide a sensitive assay for determining the immunogenic potential of such modified peptides.

The peptides used in accordance with the invention can be prepared by any method known in the art. Typically this entails programming a peptide synthesizer with a desired amino acid sequence, providing the subunits to be incorporated into the extending peptide chain, and purifying the synthesized peptide. All of these steps are well known and practiced routinely in the art. The peptides thus synthesized can incorporate modified amino acids and/or modified inter-amino acid bonds, if desired, to increase stability, reduce proteolysis, or confer some other property to the peptides. Of course, peptides may be made by other methods, including transcription and translation of a nucleic acid which encodes such peptides.

Antigens may also be expressed by the dendritic cells. For example, dendritic cells can be transfected with a nucleic acid molecule encoding the antigen or the polypeptide from which the antigen is derived. The use of a complete protein in this manner may be preferable because the host alleles can select the relevant epitope or epitopes for presentation. Host epitope selection recently was demonstrated by Zhai et al (*J. Immunol.* 156: 700–710, 1996), wherein tumor infiltrating lymphocytes recognized five different epitopes presented on the surface of cells transduced with a viral vector expressing a cancer antigen. Alternatively, the use of only a portion of a gene which does not encode a functional protein, e.g., an antigen or antigen precursor, may be preferably where it is suspected that the protein may have deleterious effects. Expressing only a portion of the gene permits vaccination against an antigen without concomitant expression of a complete functional gene product in the dendritic cells.

In preferred embodiments, the selectin polypeptide is introduced (e.g., transfected, transduced) into dendritic cells by a viral vector selected from the group consisting of adenoviruses, retroviruses, adeno-associated viruses, poxviruses including vaccinia viruses and attenuated poxviruses, lentiviruses including HIV and HIV-derived viruses, Semliki Forest virus, Venezuelan equine encephalitis virus, Sindbis virus, lambda bacteriophage and Ty virus-like particle. Examples of viruses and virus-like particles which have been used to deliver exogenous nucleic acids include: replication-defective adenoviruses (e.g., Xiang et al., *Virology* 219:220–227, 1996; Eloit et al., *J Virol* 7:5375–5381, 1997; Chengalvala et al., *Vaccine* 15:335–339, 1997), a modified retrovirus (Townsend et al., *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acad. Sci. USA* 93:11341–11348, 1996), replicative vaccinia virus (Moss, *Dev. Biol. Stand.* 82:55–63, 1994), Venezuelan equine encephalitis virus (Davis et al., *J. Virol.* 70:3781–3787, 1996), Sindbis virus (Pugachev et al., *Virology* 212:587–594, 1995) and modified bacteriophage lambda (PCT/US97/12928, WO96/21007). Antigens and/or cytokines also may be expressed in dendritic cells using such vectors.

Preferred viral vectors are replication defective. As used herein, a "replication-defective" virus or viral vector is one which is incapable of replicating autonomously in the target cell. Generally, the genome of a replication-defective adenovirus used in the context of the present invention contains mutations or deletions of at least the sequences needed for replication of the adenovirus in the infected cell. Such sequences are well known to those of ordinary skill in the art, and include, for example, in adenoviruses portions of the E1, E3, and E4 regions of the genome.

In one preferred embodiment, the virus vector is an adenovirus. An "adenovirus", for the delivery of nucleic acids encoding selectin polypeptides, refers to an adenovirus that: (1) contains exogenous genetic material that can be transcribed and translated in a mammalian cell and which encodes a polypeptide that binds a selectin ligand on endothelial cells, i.e., a selectin polypeptide, and (2) contains on its surface a ligand that selectively binds to a receptor on the surface of a target dendritic cell, and thereby gains entry to the target cell. The term adenovirus also embraces an adenovirus genome containing exogenous genetic material which encodes a polypeptide that binds a selectin ligand on endothelial cells, i.e. an unencapsidated adenovirus. As used herein, "exogenous genetic material" refers to a nucleic acid molecule (e.g., nucleic acid or oligonucleotide), either natural or synthetic, that is not naturally found in an adenovirus. The "exogenous genetic material" includes a gene or fragment thereof which encodes a polypeptide that binds a selectin ligand on endothelial cells, an antigen or precursor thereof that can, if necessary, be processed into one or more antigens, or a cytokine.

The complete nucleotide sequences of adenovirus genomes are known and have been deposited in nucleotide sequence databases. For example, the genome of the adenovirus type 5 has been completely sequenced and is accessible via GenBank accession number M73260. Similarly, portions or even whole genomes of other adenovirus types (type 2, type 7, type 12, and the like), retroviruses, and other viral vectors have also been sequenced and deposited in databases.

The nucleic acid encoding an antigen or precursor thereof preferably is inserted into a region of the virus genome which is not essential to the production of replication-defective recombinant viruses. For example, the nucleic acid preferably is not inserted into regions which contain adenovirus genes encoding proteins which are not easily supplied in trans. Thus, the nucleic acid preferably is inserted into the E1 region, which can be complemented (supplied in trans) by an adenovirus encapsidation cell line such as 293 cells. Other preferred sites of insertion of the nucleic acid include the E3 region, which is not required for production of replication-defective recombinant adenoviruses, and the E4 region, mutation of which can be complemented by co-transduction with a helper virus or plasmid or by infection of a suitable complementary cell line. Other sites also may be used as will be apparent to one of ordinary skill in the art. In particular, access to the nucleotide sequences of virus genomes enables a person skilled in the art to identify regions of the virus genomes suitable for insertion of the nucleic acid encoding a selectin polypeptide, and/or antigen or antigen precursor, and/or a cytokine.

The nucleic acids assembled to prepare a complete replication-defective virus genome or other viral or non-viral vector can be prepared by any method known in the art. For example, a virus genome or plasmid can be isolated and then modified in vitro by standard methods of molecular biology (see, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The modified virus genome so obtained optionally can be isolated and used to transfect an encapsidation cell line if necessary.

In the preferred embodiments, the virus genome further includes a regulatory sequence, e.g., a promoter region (also referred to as a "promoter"), that is operably coupled to the nucleic acid molecule encoding an antigen or antigen precursor. The regulatory sequence controls the expression of the nucleic acid molecule encoding a selectin polypeptide, and/or an antigen or antigen precursor, and/or a cytokine in the target dendritic cell. As used herein, a nucleic acid molecule encoding one or more polypeptides (the "coding sequence") and regulatory sequences are said to be "operably" joined when they are covalently linked in such a way as to place the transcription or the expression of the coding sequence under the influence or control of the regulatory sequences. If it is desired that the coding sequence be translated into a functional protein, two DNA sequences are said to be operably joined if induction of a promoter in the 5' regulatory sequence results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 3' or 5' non-transcribed and non-translated sequences involved with the initiation of transcription and translation respectively, such as a TATA box, CAAT sequence, and the like. In particular, such 5' non-transcribed regulatory sequences will include a promoter region which includes a promoter sequence for transcriptional control of the operably joined gene. Regulatory sequences can also include enhancer sequences or upstream 5' or downstream 3' transcriptional regulatory sequences as desired.

Exemplary promoters that are useful in the invention include constitutive promoters and regulatable promoters (e.g., cell lineage specific promoters, inducible promoters). Exemplary constitutive promoters include promoters derived from cytomegalovirus, a long terminal repeat (LTR) of retroviruses, e.g., Rous sarcoma virus or Moloney murine leukemia virus, and adenovirus E1A promoter, an adenovirus MLP promoter and a SRα promoter. Exemplary tissue or cell specific transcriptional regulatory sequences are those which are active in dendritic cells, including CD11a, dectins-1 and 2, MHC class II, CD1a, b or c, CD80 and CD86. Exemplary inducible promoters are described in the following references: Science 268:1786 (1995); *TIBS* 18:471 (1993); *PNAS* 91:3180 (1994); *PNAS* 90:1657 (1993); *PNAS* 88:698 (1991); *Nature Biotechnol.* 14:486 (1996); and *PNAS* 93:5185 (1996). An exemplary repressible promoter, the tetracycline repressible system, is described in PNAS 89:5547 (1992). Other constitutive, tissue-specific, inducible and repressible promoters will be known by those of skill in the art and thus are not listed here.

The expression vectors (plasmids, viruses, etc.) optionally contain one or more sequences that are suitable for use in the identification of cells that have or have not been transfected or transduced. "Transfection", as used herein, refers to the introduction of a plasmid or other non-viral nucleic acid molecule into the target cell. "Transduction", as used herein, refers to the introduction of the virus genome into the target cell. Markers to identify cells that have been transfected or transduced include, for example, genes encoding proteins that increase or decrease resistance or sensitivity to antibiotics or other compounds, genes which encode enzymes having activities that are detectable by standard assays known in the art and genes which detectably (e.g. visibly) affect the phenotype of the transduced target cells. Exemplary genes that are suitable as markers include a lacZ gene, a chloramphenicol acetyltransferase gene, an alkaline phosphatase gene, a luciferase gene, and a green fluorescent protein gene. Preferred markers are those which can be used as a basis for selection by fluorescence activated cell sorting or magnetic sorting.

Methods for delivering whole encapsidated virus include contacting dendritic cells with the virus, whereby the virus genome can be delivered by receptor-mediated endocytosis via binding of a viral capsid protein to a cellular receptor. Methods for delivering non-encapsidated viral genomes and other nucleic acid molecules such as plasmids include the foregoing methods and also methods for delivery of nucleic acids to cells familiar to those of skill in the art of molecular biology. For example, when delivering a recombinant viral genome without any associated coat protein, or an expression plasmid, the nucleic acid can be introduced into a cell by transfection using a standard technique such as electroporation, liposome transfection, calcium phosphate precipitation, or a commercially available technology such as the Tfx-50 transfection reagent (Promega Corp., Madison, Wis.).

The genetically modified or platelet modified dendritic cells of the invention can be delivered to a subject by methods known to those of ordinary skill in the art, particularly parenteral administration methods. Preferably a subject is injected intraarterially or intravenously with the modified or treated dendritic cells, or with dendritic cells that have been modified genetically and with platelets. The invention also includes administration of acitivated platelets to a subject prior to (preferably immediately prior to) or concurrently with genetically modified dendritic cells.

The invention provides other compositions and kits which are useful for practicing the above-described methods. According to another aspect of the invention, kits are provided which contain (a) nucleic acid molecules that encodes a selectin polypeptide; and optionally (b) a peptide antigen or nucleic acid encoding an antigen, and optionally, (c) a separate container of adjuvant. Instructions for the use of the nucleic acid encoding the selectin polypeptide and the antigen(s) can also be included. Other kits are like those described above except that they include instructions for preparing isolated activated platelets or membrane microparticles thereof, and treating the dendritic cells with the platelets or microparticles. Still other kits are like those described above except that they include instructions for administering isolated activated platelets or membrane microparticles thereof prior to or concurrently with genetically modified dendritic cells. The components of the kits are sufficient, when used, for example, to modify dendritic cells isolated from a subject and subsequently administered to a subject, to modulate an immune response in the subject against an antigen presented by the modified dendritic cells.

Methods for increasing or decreasing immune responses to antigens are also provided. The methods utilize the unique features of dendritic cells as antigen-presenting cells, and in particular, of modified isolated cultured dendritic cells that either express a selectin polypeptide sufficient to permit targeting to peripheral lymph nodes, and/or which have been modified by binding of activated platelets or microparticles (in vitro, ex vivo, or in vivo). These features permit enhanced presentation of antigens to T lymphocytes in lymph nodes, which under certain conditions will increase an immune response to the antigens, and under other conditions will decrease an immune response to the antigens. Thus the methods contemplate loading modified dendritic cells with antigen and using such cells for efficient delivery of antigen to the immune system.

The pharmaceutical compositions used in the methods should be sterile and contain a therapeutically effective amount of the modified dendritic cells and optionally activated platelets or microparticles thereof for modulating an immune response in a unit of weight or volume suitable for administration to a patient. In general, an effective amount is that amount of a pharmaceutical preparation that alone, or together with further doses, stimulates (or decreases) the desired response. The immune response can be measured by determining the activity of cytotoxic T lymphocytes or antige-specific antibody titers after the administration of the modified dendritic cells, and preferably both before and after the administration of the dendritic cells. Methods for measuring cytotoxic T lymphocyte activity include measurement of tumor necrosis factor release by the cytotoxic T lymphocytes and measurement of chromium release as is well known in the art. Other assays will be known to one of ordinary skill in the art and can be employed for measuring the level of the immune response following dendritic cell administration.

Where it is desired to stimulate an immune response using a therapeutic composition of the invention, this may involve the stimulation of a humoral antibody response resulting in an increase in antibody titer in serum, a clonal expansion of cytotoxic T lymphocytes, or some other desirable immunologic response. Where it is desired to inhibit an immune response using a therapeutic composition of the invention, this may involve the inhibition of a humoral antibody response resulting in a decrease in antibody titer in serum, a decrease in the number of reactive cytotoxic T lymphocytes, or some other desirable immunologic response. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

The term "pharmaceutically acceptable" means a nontoxic material that does not interfere with the effectiveness of the biological activity of the active ingredients. The term "physiologically acceptable" refers to a non-toxic material that is compatible with a biological system such as a cell, cell culture, tissue, or organism. The characteristics of carriers included in the compositions of the invention will depend on the route of administration. Physiologically and pharmaceutically acceptable carriers include diluents, fillers, salts, buffers, stabilizers, solubilizers, and other materials which are well known in the art (see, e.g., *Remington's Pharmaceutical Sciences*).

The doses of modified dendritic cell and antigen administered to a subject can be chosen in accordance with different parameters, in particular in accordance with the mode of administration used and the state of the subject. Other factors include the particular antigen used for immunization and the desired period of treatment.

EXAMPLES

Example 1

Determination of Cultured Dendritic Cell Homing to Peripheral Lymph Node

Dendritic cells (DCs) are known to have a unique and potent capacity to present antigens to naive T cells in peripheral lymph nodes (PLN). Thus dendritic cells are envisioned as ideal immunotherapeutic tools for modulating immune responses. For use in immunotherapy, large numbers of DCs are grown from CD34$^+$ progenitors or blood monocytes by in vitro differentiation. Because antigen presentation to T cells occurs in the PLN, the capacity of cultured DCs to traffic to PLN was examined.

Murine dendritic cells were grown from bone marrow progenitors as described by Mayordomo et al. (*Nature Med* 1: 1297–1302, 1995) with minor modifications. Briefly, bone marrow progenitors were isolated, red blood cells lysed, and the progenitors were cultured without depletion of lymphocytes in the presence of granulocyte-macrophage colony stimulating factor (GM-CSF; Immunex Corp.) and interleukin-4 (IL-4; R & D Systems) at 500 U/ml each in culture medium. For growth of human dendritic cells from cord blood CD34$^+$ progenitors, the culture medium included hGM-CSF (1000 U/ml), hIL-4 (50 U/ml), Flt3 ligand (100 ng/ml; Immunex Corp. and R & D Systems) and TNF-$\alpha$ (50 U/ml; R & D Systems). For growth of human dendritic cells from human monocytes (peripheral blood), the culture medium included hGM-CSF (1000 U/ml) and hIL-4 (1000 U/ml). For observation, DCs were fluorescently labeled with calcein (2.5 $\mu$g/ml/10$^7$ cells; Molecular Probes, Inc.).

The migration of the cultured dendritic cells was observed after intravenous injection. When injected intravenously, DCs did not reach the PLN, but rather accumulated in extranodal sites, mainly spleen and liver.

Example 2

Determination of L-selectin Expression on Cultured Dendritic Cells

DC homing to PLN from blood is mediated by DC cell surface L-selectin binding to selectin ligands (peripheral node addressing, PNAds) on high endothelial venules (HEV). The expression of L-selectin and binding of the cultured DCs to PNAds were examined to determine if the defect in PLN homing of DCs was due to inefficient binding of DCs to HEV.

Dendritic cell binding to PNAds was examined in a parallel plate flow chamber assay described by Lawrence and Springer (*Cell* 65:859–873, 1991). DCs were cultured under a variety of conditions including those described above with or without several concentrations of TGF-$\beta$, IL-3 and inhibitors of metalloproteinases.

Regardless of the progenitor cell used (human CD34$^+$ cells, human monocytes or murine bone marrow progenitors) or culture conditions, cultured DCs did not express L-selectin after 2–3 days of culture as determined by FACS analysis with anti-L-selectin antibody (anti-mouse L-selectin from PharMingen; anti-human L-selectin from Coulter Immunotech), and could neither tether nor roll on PNAd-coated surfaces (i.e. bind selectin ligands) in the parallel plate flow chamber assay.

Example 3

Expression of E/L-Selectin Chimera Restores Selectin Ligand Binding by DCs

To restore L-selectin expression, a retroviral construct containing human L-selectin (GenBank accession number X16150), was prepared according to standard procedures. A modified murine leukemia virus was generated by transfection of the 293GPG retroviral packaging cell line (Ory et al., *Proc. Natl. Acad. Sci. USA* 93:11400–11406, 1996). The retrovirus efficiently transduced murine DCs.

Murine bone marrow derived DCs were transduced with the L-selectin-expressing retrovirus on days 2 and 4 or culture and tested at day 7 or 8. Analysis of surface L-selectin expression by antibody recognition in transduced DCs showed that very few DCs expressed L-selectin protein.

As it is known that L-selectin can be rapidly degraded from the cell surface by metalloproteinases, another retroviral construct that expressed an E/L-selectin chimera (von Andrian et al., *Cell* 82:989–999, 1995; Stein et al. *J. Exp. Med.* 189:37–49, 1999) was prepared as above. The chimeric protein contains the transmembrane and intracellular domains of L-selectin and the extracellular domain of E-selectin. DCs were transduced as described above. In contrast, 15–30% of DCs transduced with the E/L-selectin chimera expressed the chimeric protein as recognized by a monoclonal anti-human E-selectin antibody (Southern Biotechnology).

The E/L-selectin transduced DCs were able to tether and roll both in vitro and in vivo on PNAd, as observed with the parallel plate flow chamber assay and using intravital microscopy, respectively.

Example 4

DC Binding to PNAd is Restored by Activated Platelets

Next it was determined whether DCs can bind activated platelets and if so whether the DC-platelet could tether and roll on PNAd. Platelets were activated with thrombin receptor activating protein (TRAP; Bachem, Pa.; 25 $\mu$m for 5 min) or thrombin (Sigma Chemical Co., St. Louis, Mo.; 0.5 U/ml for 5 min) according to standard procedures (see, e.g., Diacovo et al., 1996). Fluorescently-labeled activated platelets (murine and human) were incubated with fluorescently-labeled murine DCs and binding was observed with a fluorescence activated cell sorter and confocal microscopy. DCs readily bound to activated platelets. Preincubation of cultured DCs with activated platelets also conferred the capacity to tether and roll on PNAd in the parallel plate flow chamber assay. Microscopy confirmed that activated platelets were bound to the rolling DCs. Activated platelets also mediate rolling of DCs in mouse high endothelial venules in vivo as observed by intravital microscopy.

Example 5

Localization of Selectin Expression on Dendritic Cells

Murine bone marrow-derived dendritic cells were transformed with the E/L-selectin-expressing CMMP retrovirus as described above and then stained with mouse-anti-human E-selectin monoclonal antibody CL37 (20 $\mu$g/ml; mouse IgG; Dr. C. Wayne Smith, Baylor College). Subsequently, the cells were washed and stained with 12 nm colloidal gold conjugated goat-anti-mouse antibody (dilution 1:6; Jackson Labs). The cells were fixed and prepared for low-voltage scanning electron microscopy (LVSEM) and analyzed in the electron microscopy core facility at the University of Minnesota as described in by von Andrian et al. (*Cell* 82:989–999, 1995).

FIG. 1 is a digitized low-voltage scanning electron micrograph showing the surface of a murine bone marrow-derived dendritic cell at 80,000× magnification. The length of the dotted bar within the black band at the bottom of the image is 380 nm. The clusters of bright white dots on the ridges and tips of microvilli are gold particles delineating E/L-selectin expression. A quantitative analysis of gold particle distribution on three representative cells indicates that 80–95% of particles are associated with microvilli, and of these, ~75% are found on the upper half and the tip. There was no detectable staining on untransformed cells and no binding was detected on transformed cells when an isotype-matched non-binding control antibody was used. The data are remarkably consistent with previous studies using E/L-selectin transfected pre-B cells (von Andrian et al., *Cell* 82:989–999, 1995).

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference.

What is claimed is:

1. A method for delivery of dendritic cells to a secondary lymphoid tissue of a subject, wherein selectin ligand molecules are expressed on cells of the secondary lymphoid tissue, comprising
    providing isolated dendritic cells which are genetically modified to express on the cell surface an E/L-selectin chimera that contains the transmembrane and intracellular domains of L-selectin and the extracellular domain of E-selectin, and
    administering the isolated genetically modified dendritic cells to the subject.

2. The method of claim 1, wherein the step of providing isolated dendritic cells comprises isolating dendritic cells from the subject and transfecting the isolated dendritic cells with a nucleic acid molecule which encodes the E/L-selectin chimera.

3. The method of claim 1, wherein the step of providing isolated dendritic cells further comprises treating the isolated transfected dendritic cells with isolated activated platelets or membrane microparticles thereof which contain P selectin.

4. The method of claim 1, wherein the isolated dendritic cells are administered intravenously.

5. A method for delivery of dendritic cells to a non-lymphoid tissue of a subject where selectin ligands are expressed on endothelial cells of the non-lymphoid tissue, comprising
    providing isolated dendritic cells which are genetically modified to express on the cell surface an E/L-selectin chimera that contains the transmembrane and intracellular domains of L-selectin and the extracellular domain of E-selectin, and
    administering the isolated genetically modified dendritic cells to the subject.

6. A method for delivery of dendritic cells to a secondary lymphoid tissue of a subject, wherein selectin ligand molecules are expressed on cells of the secondary lymphoid tissue, comprising
    providing isolated dendritic cells,
    treating the isolated dendritic cells in vitro or ex vivo with isolated activated platelets to form platelet modified dendritic cells, and
    administering the isolated platelet modified dendritic cells to the subject.

7. The method of claim 6, wherein the step of providing isolated dendritic cells further comprises culturing the isolated dendritic cells to expand the isolated dendritic cells.

8. The method of claim 6, wherein the isolated platelet modified dendritic cells are administered intravenously.

9. A method for delivery of dendritic cells to a non-lymphoid tissue of a subject where selectin ligands are expressed on endothelial cells of the non-lymphoid tissue, comprising
    providing isolated dendritic cells,
    treating the isolated dendritic cells in vitro or ex vivo with isolated activated platelets to form platelet modified dendritic cells, and
    administering the isolated platelet modified dendritic cells to the subject.

10. The method of claim 9, wherein the step of providing isolated dendritic cells further comprises culturing the isolated dendritic cells to expand the isolated dendritic cells.

11. The method of claim 9, wherein the isolated platelet modified dendritic cells are administered intravenously.

12. A composition comprising isolated dendritic cells which are genetically modified to express on the cell surface an E/L-selectin chimera that contains the transmembrane and intracellular domains of L-selectin and the extracellular domain of E-selectin.

13. The composition of claim 12, wherein the amount of the E/L-selectin chimera expressed on the cell surface is greater than the naturally occurring amount of a selectin polypeptide expressed on the cell surface in vitro and is sufficient to target the genetically modified dendritic cells to peripheral lymph nodes.

14. A composition comprising the composition of claim 12 and an antigen, wherein the dendritic cells are loaded with or transfected to express the antigen.

15. A composition comprising isolated dendritic cells, isolated activated platelets or membrane microparticles thereof which contain P selectin and an antigen, wherein the dendritic cells are loaded with or transfected to express the antigen.

16. A method for stimulating an immune response to an antigen in a subject comprising
    administering to the subject the composition of claim 14.

* * * * *